(12) United States Patent
Mabuchi et al.

(10) Patent No.: US 8,663,278 B2
(45) Date of Patent: Mar. 4, 2014

(54) ORGAN FIXING EQUIPMENT (75) Inventors: Hitoshi Mabuchi, Fukuroi (JP);
Shigeaki Funamura, Fukuroi (JP)

(73) Assignee: Covidien LP, Mansfield, MA (US)

( * ) Notice: Subject to any disclaimer, the term of this patent is extended or adjusted under 35 U.S.C. 154(b) by 962 days.

(21) Appl. No.: 11/576,873

(22) PCT Filed: Oct. 6, 2005

(86) PCT No.: PCT/EP2005/010774
§ 371 (c)(1),
(2), (4) Date: Jul. 3, 2008

(87) PCT Pub. No.: WO2006/037639
PCT Pub. Date: Apr. 13, 2006

(65) Prior Publication Data
US 2009/0163939 A1  Jun. 25, 2009

(30) Foreign Application Priority Data
Oct. 6, 2004  (JP) .................................. 2004-294258

(51) Int. Cl.
A61B 17/04  (2006.01)

(52) U.S. Cl.
USPC ............................ 606/228; 606/139; 606/232

(58) Field of Classification Search
USPC ......... 606/139, 138, 228, 215, 232, 229, 230, 606/231; 87/3, 8; 24/131 C
See application file for complete search history.

(56) References Cited

U.S. PATENT DOCUMENTS

| | | |
|---|---|---|
| 2,012,776 A | 8/1935 | Roeder |
| 4,775,121 A | 10/1988 | Carty |
| 4,935,027 A | 6/1990 | Yoon |
| 5,037,433 A | 8/1991 | Wilk |
| 5,052,396 A | 10/1991 | Wedel et al. |
| 5,100,387 A | 3/1992 | Ng |
| 5,123,914 A | 6/1992 | Cope |
| 5,226,892 A | 7/1993 | Boswell |
| 5,242,427 A | 9/1993 | Bilweis |
| 5,251,873 A | 10/1993 | Atkinson et al. |
| 5,281,237 A | 1/1994 | Gimpelson |
| 5,330,488 A | 7/1994 | Goldrath |
| 5,336,229 A | 8/1994 | Noda |

(Continued)

FOREIGN PATENT DOCUMENTS

| | | |
|---|---|---|
| DE | 2900265 A1 | 7/1980 |
| JP | 61205510 U | 12/1986 |

(Continued)

OTHER PUBLICATIONS

Partial International Search Report for International Application No. PCT/EP2005/010774 dated Dec. 28, 2005.

*Primary Examiner* — Ryan Severson
*Assistant Examiner* — Anh Dang (57) ABSTRACT

An organ fixing equipment includes a securing part formed by bundling a suturing thread into a bar, and a fixing part composed of the suturing thread forming the securing part and a continuous suturing thread. By pulling the fixing part relative to the securing part with a force of not less than a predetermined magnitude, the suturing thread forming the securing part can be unraveled. A set of organ fixing equipment is provided with an insertion equipment, for inserting the organ fixing equipment and taking-out equipment for taking out the organ fixing equipment from the patient body.

8 Claims, 10 Drawing Sheets (56) References Cited

U.S. PATENT DOCUMENTS

| | | |
|---|---|---|
| 5,336,231 A | 8/1994 | Adair |
| 5,363,539 A | 11/1994 | Tisol |
| 5,364,410 A | 11/1994 | Failla et al. |
| 5,389,082 A | 2/1995 | Baugues et al. |
| 5,391,182 A | 2/1995 | Chin |
| 5,462,560 A | 10/1995 | Stevens |
| 5,499,991 A | 3/1996 | Garman |
| 5,501,691 A | 3/1996 | Goldrath |
| 5,531,699 A | 7/1996 | Tomba et al. |
| 5,562,684 A | 10/1996 | Kammerer |
| 5,626,590 A | 5/1997 | Wilk |
| 5,643,295 A | 7/1997 | Yoon |
| 5,653,716 A | 8/1997 | Malo |
| 5,665,096 A | 9/1997 | Yoon |
| 5,681,333 A | 10/1997 | Burkhart |
| 5,722,981 A | 3/1998 | Stevens |
| 5,728,109 A * | 3/1998 | Schulze et al. ............. 606/139 |
| 5,741,276 A | 4/1998 | Poloyko et al. |
| 5,782,845 A | 7/1998 | Shewchuk |
| 5,795,335 A | 8/1998 | Zinreich |
| 5,817,111 A | 10/1998 | Riza |
| 5,895,395 A | 4/1999 | Yeung |
| 5,897,563 A | 4/1999 | Yoon et al. |
| 5,921,993 A | 7/1999 | Yoon |
| 5,938,668 A | 8/1999 | Scirica et al. |
| 5,993,434 A | 11/1999 | Dev et al. |
| 6,022,360 A | 2/2000 | Reimels |
| 6,036,700 A | 3/2000 | Stefanchik et al. |
| 6,066,146 A | 5/2000 | Carroll et al. |
| 6,110,183 A | 8/2000 | Cope |
| 6,113,068 A | 9/2000 | Ryan |
| 6,113,610 A | 9/2000 | Poncet |
| 6,113,611 A | 9/2000 | Allen et al. |
| 6,156,056 A | 12/2000 | Kearns et al. |
| 6,451,024 B1 | 9/2002 | Thompson et al. |
| 6,500,184 B1 | 12/2002 | Chan et al. |
| 6,524,317 B1 | 2/2003 | Ritchart et al. |
| 6,638,286 B1 | 10/2003 | Burbank et al. |
| 7,306,613 B2 | 12/2007 | Kawashima et al. |
| 7,320,693 B2 | 1/2008 | Pollack et al. |
| 7,731,726 B2 | 6/2010 | Belhe et al. |
| 7,918,868 B2 | 4/2011 | Marshall et al. |
| 2002/0147456 A1 | 10/2002 | Diduch et al. |
| 2003/0004523 A1 | 1/2003 | Chan et al. |
| 2003/0109883 A1 | 6/2003 | Matsuzaki et al. |
| 2003/0191497 A1 | 10/2003 | Cope |
| 2004/0039442 A1 | 2/2004 | St. Goar et al. |
| 2004/0098050 A1 | 5/2004 | Foerster et al. |
| 2004/0122473 A1 | 6/2004 | Ewers et al. |
| 2004/0249393 A1 | 12/2004 | Weisel et al. |
| 2004/0249395 A1 | 12/2004 | Mikkaichi et al. |
| 2005/0253033 A1 | 11/2005 | Mizukoshi et al. |
| 2005/0288689 A1 | 12/2005 | Kammerer et al. |
| 2006/0069398 A1 | 3/2006 | Suzuki et al. |
| 2007/0023305 A1 | 2/2007 | Chan et al. |
| 2007/0118153 A1 | 5/2007 | Funamura et al. |
| 2007/0179509 A1 | 8/2007 | Nagata et al. |
| 2007/0293876 A1 | 12/2007 | Abe et al. |
| 2008/0228204 A1 | 9/2008 | Hamilton et al. |
| 2008/0243147 A1 | 10/2008 | Hamilton et al. |

FOREIGN PATENT DOCUMENTS

| | | |
|---|---|---|
| JP | 4226643 A | 8/1992 |
| JP | 05-161655 | 6/1993 |
| JP | 06-024533 B | 4/1994 |
| JP | 06044511 U | 6/1994 |
| JP | 07-328020 | 12/1995 |
| JP | 2002336262 A | 11/2002 |
| JP | 2004141646 A | 5/2004 |
| JP | 2005270332 A | 10/2005 |
| JP | 2006025932 | 2/2006 |
| JP | 2006025933 | 2/2006 |
| JP | 2006025934 | 2/2006 |
| JP | 2006151429 | 5/2006 |
| WO | 9421178 A1 | 9/1994 |
| WO | 95/22932 A1 | 8/1995 |
| WO | 03/065903 A1 | 8/2003 |
| WO | 2004006782 A1 | 1/2004 |
| WO | 2006037639 A1 | 4/2006 |
| WO | 2006082810 A1 | 8/2006 |
| WO | 2007018520 A1 | 2/2007 |

* cited by examiner

ORGAN FIXING EQUIPMENT

CROSS-REFERENCE TO RELATED APPLICATIONS

This application is based on and claims the benefit of International (PCT) Application Serial No. PCT/EP2005/010774, filed Oct. 6, 2005, which claims priority from Japanese Patent Application No. 2004-294258, filed Oct. 6, 2004, both of which are herein incorporated by reference in their entirety.

FIELD OF THE INVENTION

The present invention relates to devices for temporary-restraint of bodily tissue, and to an organ fixing equipment to be used for fixing a predetermined organ in the body of a patient, on a skin side portion, and an organ fixing equipment set.

BACKGROUND OF THE INVENTION

In the prior art, an organ fixing equipment set having an organ fixing equipment has been used for fixing a portion to be sutured in the body of a patient, especially the skin and an organ such as an internal organ. For example, a person having a function lowered to swallow a food from the mouth due to age or disease is fed with a liquid food or drink such as a nutriment by means of a gastrostomy tube. This gastrostomy tube is attached by forming a hole in the abdomen of a patient. In order to attach the gastrostomy tube properly in that case, the abdomen wall and the stomach wall are fixed in advance by means of the organ fixing equipment set having the organ fixing equipment (See JP-A-5-161655, for example).

This organ fixing equipment set is provided with two piercing needles disposed in parallel at a spacing. In case the abdomen wall and the stomach wall are to be fixed, the two piercing needles are simultaneously pierced at first into a portion to be sutured of the patient. Next, the suturing thread is threaded into one piercing needle, and an internal needle having a loop of a wire connected to its leading end portion is threaded into the other piercing needle. The internal needle is extracted from the piercing needle in the state where the suturing thread is entangled with the loop in the stomach wall. In the state where the leading end portion of the suturing thread is being protruded from the other piercing needle, the two piercing needles are extracted from the portion to be sutured, and the two side portions of the suturing thread protruding to the outside of the body of the patient are bound to fix the abdomen wall and the stomach wall completely.

However, the aforementioned organ fixing equipment set of the prior art is troubled by a problem that the operations are complicated, because it is necessary to pierce the two piercing needles simultaneously and to thread the internal needle or the suturing thread into the individual piercing needles. If, on the other hand, the insertion of the piercing needle into the internal needle is not skillful, the protruding direction or shape of the loop is not proper, and the suturing thread may not be entangled. This raises a problem that the operations need skills. In case, on the other hand, a sufficient space is not on the inner side of the portion to be sutured, there arises a problem that it is difficult and less reliable to entangle the suturing thread by the loop.

SUMMARY OF THE INVENTION

In one aspect of the present invention, an organ fixing equipment for fixing a predetermined organ in the body of a patient on a skin side wall portion comprises a securing part formed by bundling a suturing thread into a bar. The securing part is adapted to be disposed on the inner wall side of the organ. A fixing part has the suturing thread forming the securing part and a continuous suturing thread. The fixing part extends to the outside of the body of the patient from the substantial center in the axial direction of the securing part through a hole portion formed in the organ and in the skin side wall portion.

In another aspect, a device for temporary restraint of bodily tissue is formed from a length of suture. One end of the length is a coil portion. The other end is a pulling portion and an intermediate portion is a core portion formed by repeatedly-doubling back successive short lengths of the suture so as to form a bar in which many suture lengths lie parallel to each other. The coil portion is radially around the core portion and the pulling portion emerges from the coil portion at an intermediate point along the length of the bar in the manner of the vertical stroke below the horizontal bar of the letter.

DETAILED DESCRIPTION OF THE DRAWINGS

Figure 1:
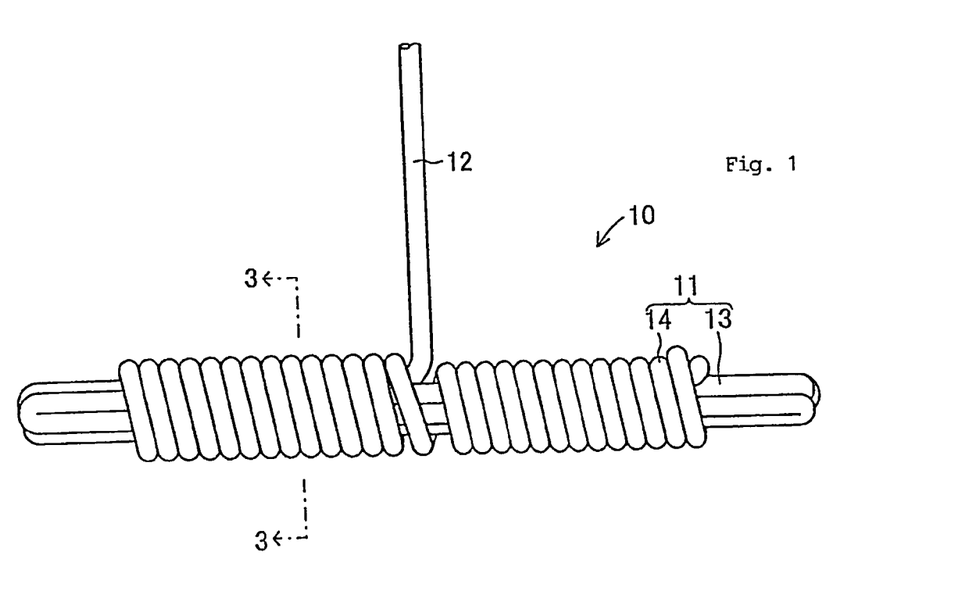
FIG. 1 is a front elevation showing an organ fixing equipment according to one embodiment of the invention.

One embodiment of the invention will be described in detail with reference to the accompanying drawings. FIG. 1 shows an organ fixing equipment 10 according to the same embodiment. This organ fixing equipment 10 is used for fixing the abdominal wall A and the stomach wall B (as referred to FIG. 6 and so on) of a patient, for example, by suturing them. The organ fixing equipment 10 is constituted of a securing part 11 formed in a bar, and a fixing part 12 extending perpendicularly of the securing part 11 from the axial central portion of the securing part 11. The organ fixing equipment 10 is shaped into a letter "T" such that the bar-shaped securing part 11 is formed by bundling a suturing thread of nylon whereas the fixing part 12 is formed by extending the end portion side of the suturing thread at a right angle with respect to the securing part 11 from the central portion of the suturing thread.

Figure 2:
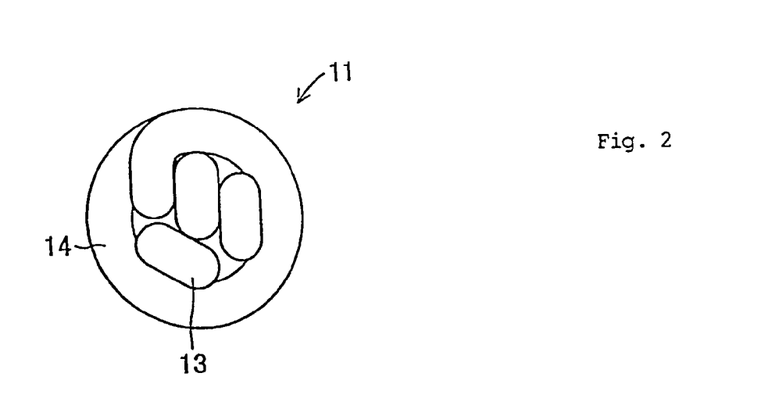
FIG. 2 is a side elevation of the organ fixing equipment shown in FIG. 1.
Figure 3:
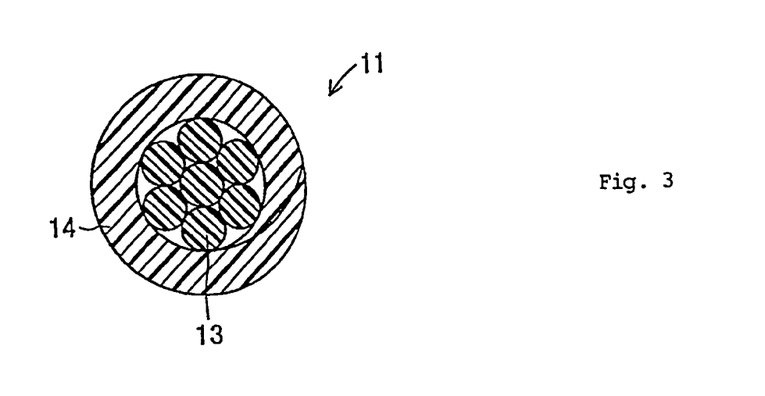
FIG. 3 is a section along 3-3 of FIG. 1.

The securing part 11 is constituted such that a core portion 13 is formed by bundling the suturing thread in a manner to fold back one end side portion of the suturing thread a plurality of times whereas a coil portion 14 is formed by winding the suturing thread around the core portion 13. FIG. 2 shows a side face of the securing part 11, and FIG. 3 shows a section of the securing part 11. On the other hand, the fixing part 12 extends from the central portion of the securing part 11, and its end portion on the side of the securing part 11 is so linked to the core portion 13 that it is fastened in the coil portion 14. In the organ fixing equipment 10 thus constituted, when the fixing part 12 is pulled relative to the securing part 11 with a predetermined force or more, the core portion 13 sequentially comes out of the coil portion 14 so that the suturing thread forming the securing part 11 is unraveled.

Figure 4:
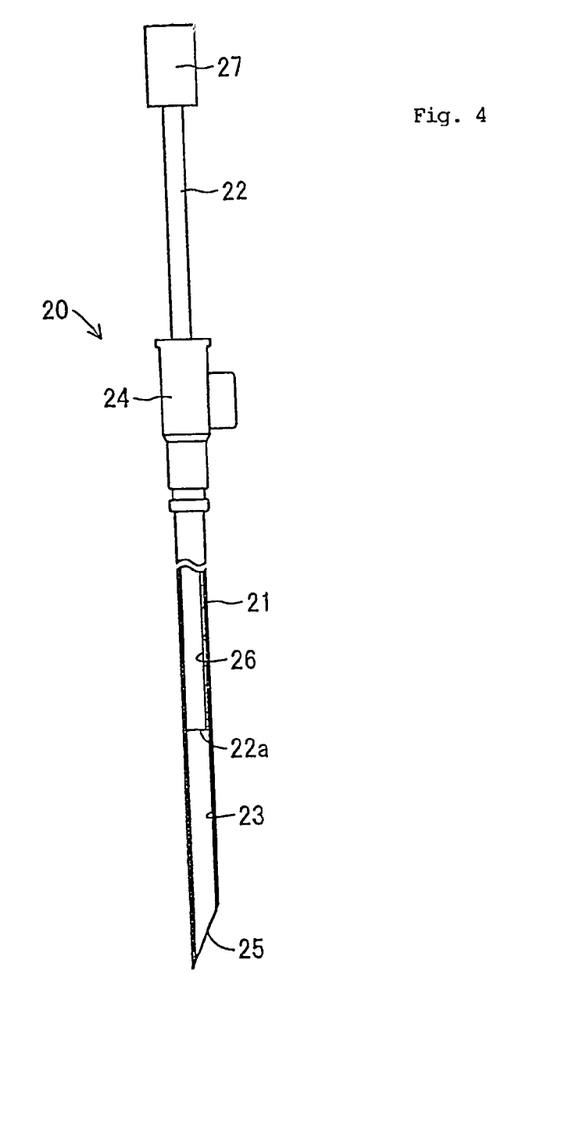
FIG. 4 is a partially cut-away section showing an insertion equipment.

When this organ fixing equipment 10 is to be attached to the abdomen of a patient, an insertion equipment 20 is used, as shown in FIG. 4. This insertion equipment 20 is constituted of a piercing needle 21 to be inserted, and a cylindrical protrusion portion 22 to be inserted into the piercing needle 21. The piercing needle 21 is formed of a cylinder of a metal having a through bore 23 therein, and a grip portion 24 is attached to the base end portion (i.e., an upper end portion in FIG. 4). This grip portion 24 is formed into such a cylindrical shape as has a larger diameter on its upper portion side and a smaller diameter on its lower portion side, and is provided therein with a (not-shown) guide hole communicating with the through bore 23.

This guide hole has a diameter set larger than that of the through bore 23 so that the cylindrical protrusion portion 22 is easily inserted from the upper end portion of the piercing needle 21. On the other hand, the diameter of the through bore 23 is set to such a size that the securing part 11 and the fixing part 12 of the organ fixing equipment 10 can be inserted in a straight shape. Moreover, the piercing needle 21 is cut sharp at its leading end portion 25 in a direction oblique to the axial direction and directed at its opening in the transverse direction.

The cylindrical protrusion portion 22 is constituted of a cylindrical member formed of a metal and having a through bore 26 therein, and a grip portion 27 is attached to the base end portion (or the upper end portion) of the cylindrical protrusion portion 22. In the grip portion 27, moreover, there is formed the (not-shown) guide hole which communicated with the through bore 26. Moreover, the cylindrical protrusion portion 22 has an external diameter set to such a size as can be inserted into the through bore 23 of the piercing needle 21, and the through bore 26 has a diameter set to such a size as can pass the fixing part 12 but not the securing part 11 therethrough.

When the organ fixing equipment 10 is to be attached to the insertion equipment 20 thus constituted, the securing part 11 is longitudinally inserted at first from the upper end side of the through bore 23 into the through bore 23 of the piercing needle 21, from which the cylindrical protrusion portion 22 has been taken out. Next, the leading end portion of the fixing part 12 is inserted from the leading end opening of the cylindrical protrusion portion 22 and is protruded from the upper end portion of the guide hole of the grip portion 27. Then, the leading end portion 22a of the cylindrical protrusion portion 22 in this state is inserted from the upper end portion of the guide hole of the grip portion 24 so that the cylindrical protrusion portion 22 is inserted into the piercing needle 21.

Figure 5:
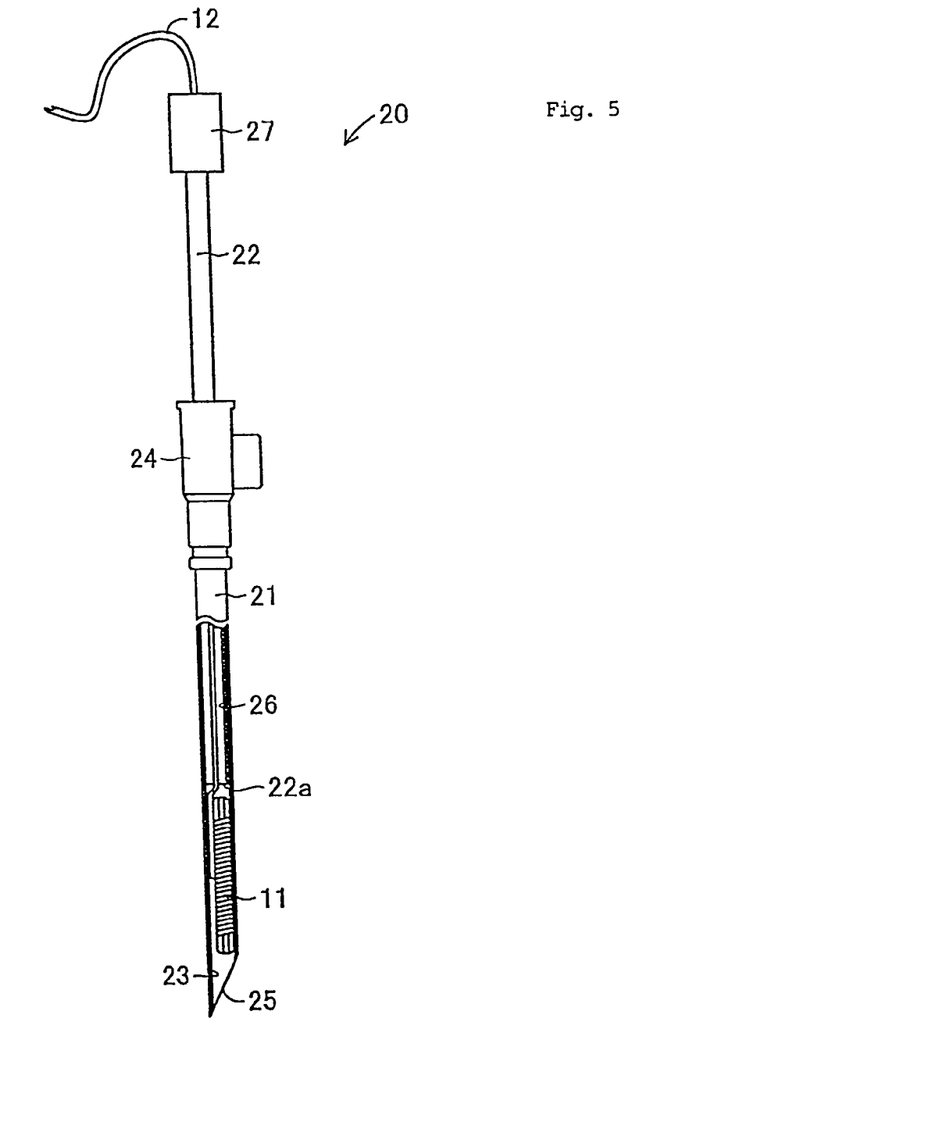
FIG. 5 is a partially cut-away section showing the state where the organ fixing equipment is attached to the insertion equipment shown in FIG. 4.

At this time, the fixing part 12 is lightly pulled on its end portion side so that it may not become slack. Then, the cylindrical protrusion portion 22 is moved, while pushing the securing part 11 with its leading end portion 22a, toward the side of the leading end portion 25 of the piercing needle 21. This insertion of the cylindrical protrusion portion 22 is stopped in the state of FIG. 5, when the leading end portion of the securing part 11 (i.e., the lower end portion inserted into the through bore 23) comes to the vicinity of the leading end portion of the through bore 23.

Figure 6:
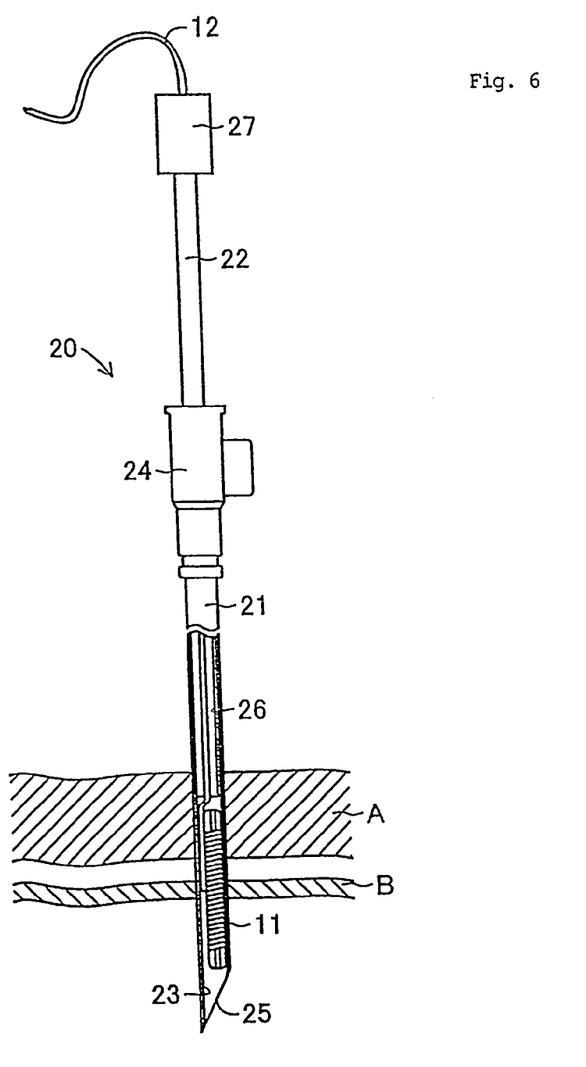
FIG. 6 is a section showing the state where the insertion equipment shown in FIG. 5 is pierced into an abdomen.
Figure 7:
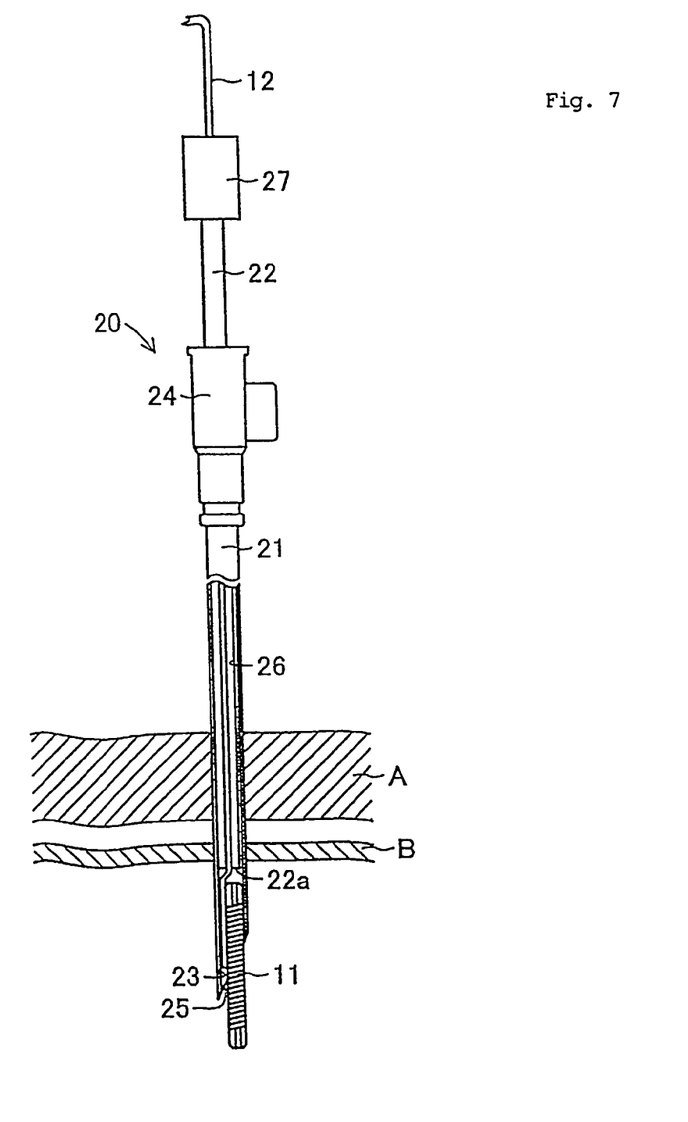
FIG. 7 is a section showing the state where a securing part is pushed out into the inside of a stomach wall by a cylindrical protrusion portion.

Next, the insertion equipment 20 thus having the organ fixing equipment 10 attached thereto is pierced from the skin surface into the abdomen of the patient thereby to pass the piercing needle 21 through the abdomen wall A and the stomach wall B, as shown in FIG. 6. In this case, the insertion equipment 20 is pushed so far that the opening of the leading end portion 25 of the piercing needle 21 comes to the inner side of the stomach wall B. Next, the cylindrical protrusion portion 22 is pushed to the inner side of the piercing needle 21 thereby to protrude the securing part 11 from the leading end portion 25 of the piercing needle 21, as shown in FIG. 7.

Figure 8:
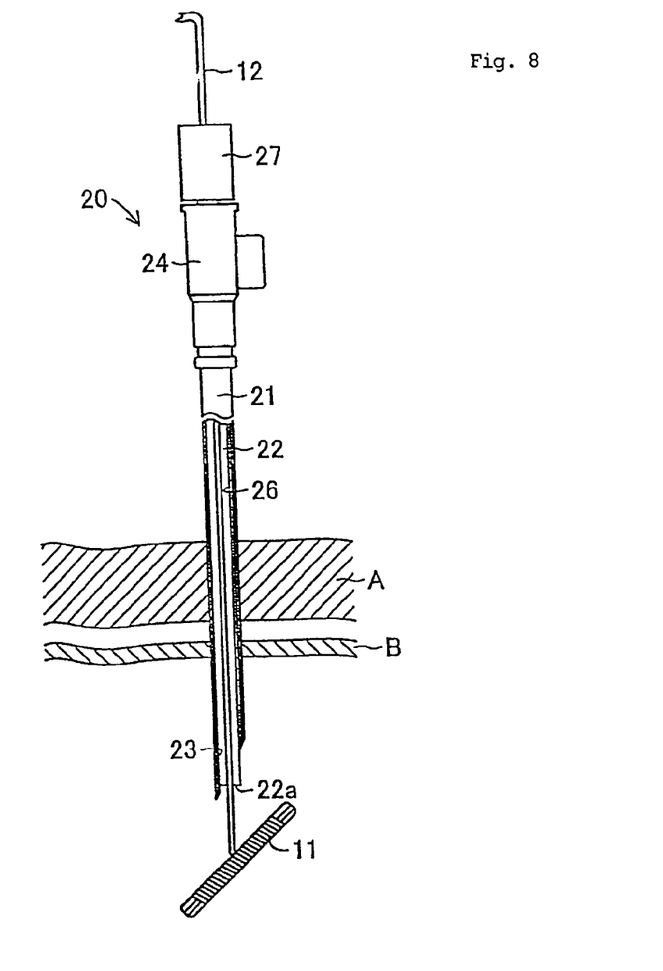
FIG. 8 is a section showing the state where the securing part is pushed into the inside of the stomach wall.
Figure 9:
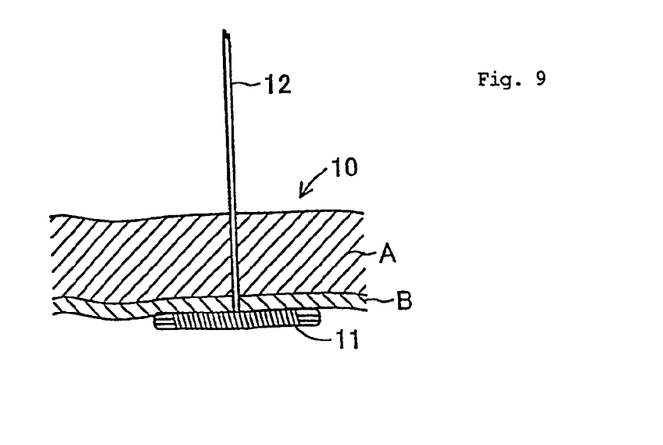
FIG. 9 is a section showing the state where the securing part engages with the inside of the stomach wall.

Then, the cylindrical protrusion portion 22 is further pushed into the inside of the piercing needle 21 thereby to position its leading end portion 22a at the leading end portion 25 of the piercing needle 21, as shown in FIG. 8. As a result, the securing part 11 is pushed to the outside of the piercing needle 21 so that it is positioned on the inner side of the stomach wall B. In this state, the piercing needle 21 is pulled together with the cylindrical protrusion portion 22 while leaving the organ fixing equipment 10 in the body of the patient, so that it is pulled out from the body of the patient. At this time, the securing part 11 extends transversely along the stomach wall B into engagement with the stomach wall B, as shown in FIG. 9.

Figure 10:
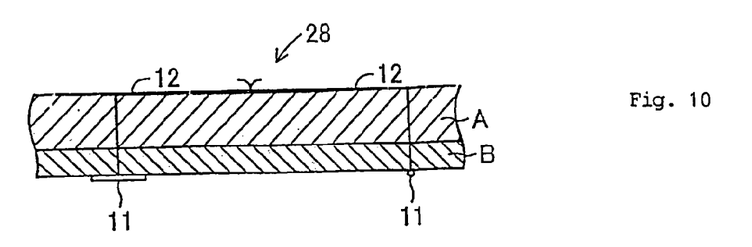
FIG. 10 is a section showing the state where the stomach wall is fixed on an abdomen wall by a sutured portion.
Figure 11:
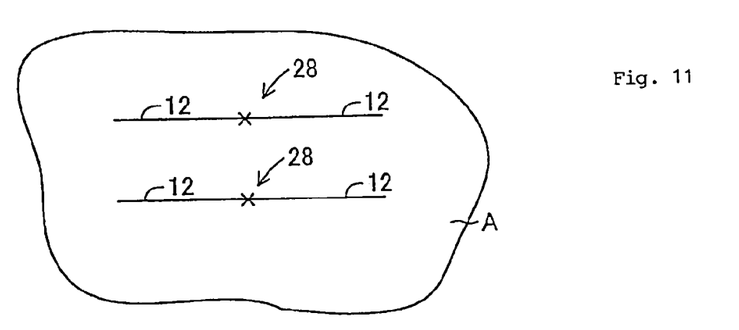
FIG. 11 is a top plan view showing the state where two sutured portions are formed in the abdomen.

Next, another organ fixing equipment 10 is thus attached by repeating the aforementioned operations to the vicinity of the organ fixing equipment 10 in the abdomen portion of the patient having the organ fixing equipment 10 attached thereto. Then, the end portions of the fixing parts 12 of the organ fixing equipment 10 extending to the outside of the body of the patient are tied to form sutured portions 28, as shown in FIG. 10. As a result, the stomach wall B is fixed on the abdomen wall A. Alternatively, other sutured portions 28 can also be formed, if necessary, in the vicinity of the sutured portion 28, as shown in FIG. 11. In the state where the stomach wall B is fixed on the abdomen wall A, the following operations are performed to attach a gastrostomy tube or the like.

Figure 12:
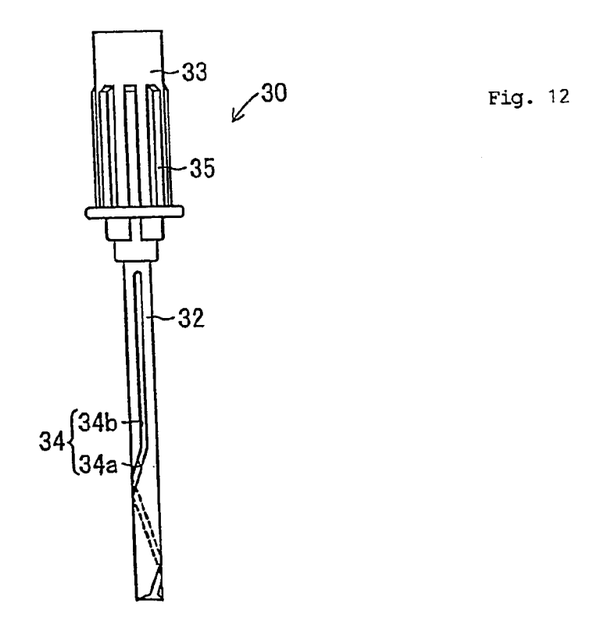
FIG. 12 is a front elevation showing a taking-out equipment.
Figure 13:
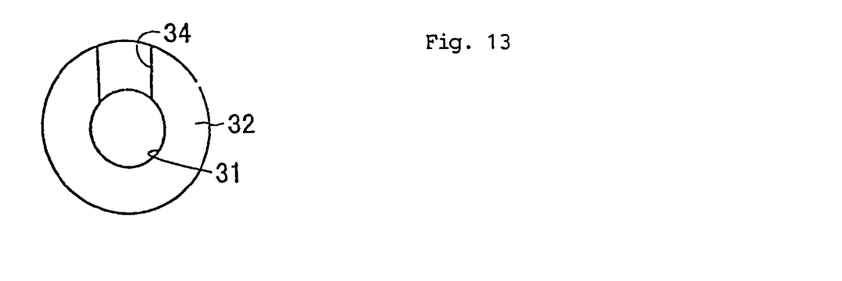
FIG. 13 is a bottom view of FIG. 12.

When the organ fixing equipment 10 is to be taken out from the body of the patient after the predetermined operations were ended, moreover, a taking-out equipment 30 shown in FIG. 12 is employed. This taking-out equipment 30 is constituted of a cylindrical portion 32 made of a metal and having a bore 31 formed therein (as referred to FIG. 13), and a grip portion 33 disposed at the base end portion of the cylindrical portion 32. In the cylindrical portion 32, moreover, there is formed a groove portion 34, which extends between the outer circumference and the inner circumference from the lower end portion to the upper end portion. This groove portion 34 is provided at its lower side portion with a helical groove 34a extending axially while turning in the circumferential direction and at its upper side portion with a straight groove 34*b* extending axially. Moreover, the grip portion 33 is formed into a column shape having a slip preventing fringe 35 on its circumference.

Figure 14:
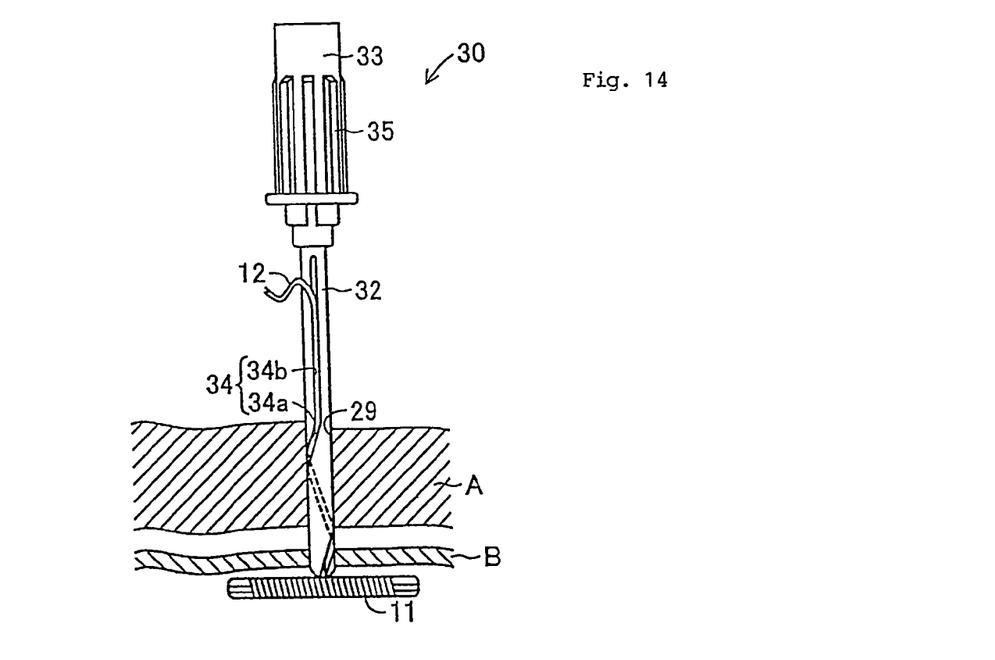
FIG. 14 is a section showing the state where the taking-out equipment is inserted along the fixing part into a hole portion.

When the organ fixing equipment 10 is to be taken out from the patient body by using the taking-out equipment 30 thus constituted, the exposed portion of the fixing part 12 from the sutured portion 28 is cut at first so that the end portion of the fixing part 12 of the organ fixing equipment 10 is released. Next, as shown in FIG. 14, the lower end portion of the groove portion 34 is applied to the fixing part 12, and this fixing part 12 is wound, while its portion being inserted in the groove portion 34, on the circumference of the cylindrical portion 32 of the taking-out equipment 30 and is inserted in the groove portion 34, and the cylindrical portion 32 is inserted into a hole portion 29 formed in the abdomen wall A and the stomach wall B.

Figure 15:
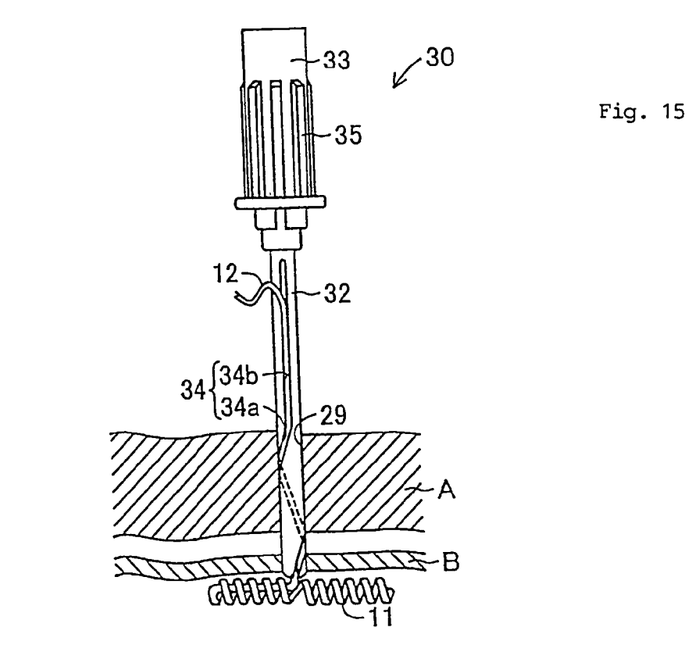
FIG. 15 is a section showing the state where the securing part is unraveled.
Figure 16:
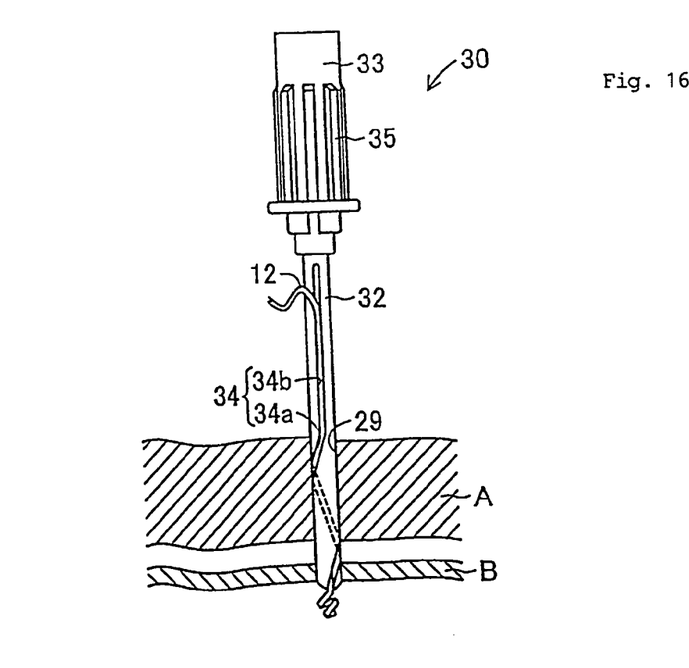
FIG. 16 is a section showing the state where the organ fixing equipment having the unraveled securing part is taken out.

Next, when the leading end portion of the cylindrical portion 32 contacts with the securing part 11, the insertion of the cylindrical portion 32 into the hole portion 29 is stopped, and the fixing part 12 is pulled while the taking-out equipment 30 is held stationary. As a result, the core portion 13 of the securing part 11 comes out of the coil portion 14 so that the securing part 11 is unraveled. By further pulling the fixing part 12, moreover, the securing part 11 unraveled is sequentially taken out through the inside of the cylindrical portion 32 to the outside, as shown in FIG. 16. When all the suturing threads constituting the organ fixing equipment 10 are taken out, the taking-out equipment 30 is pulled out from the body of the patient. Likewise, the remaining organ fixing equipments 10 are taken out from the patient body thereby to end the taking-out operations of the organ fixing equipment 10. Here, in this embodiment, the organ fixing equipment 10, the insertion equipment 20 and the taking-out equipment 30 constitute a set of organ fixing equipment according to the invention.

In this organ fixing equipment 10 thus far described, one suturing thread is bundled to form the bar-shaped securing part 11 and the fixing part 12. When the securing part 11 is positioned inside of the stomach wall B, the securing part 11 extends along the inner wall of the stomach wall B, and the securing part 11 and the fixing part 12 are formed into the T-shape so that the end portion side portion of the fixing part 12 protrudes to the outside of the patient body. By attaching the two organ fixing equipments 10 to the predetermined positions of the abdomen and by joining the fixing parts 12 protruding to the outside of the body, therefore, the sutured portions 28 can be formed to fix the stomach wall B on the abdomen wall A. When the organ fixing equipment 10 is to be taken out, the organ fixing equipment 10 can be taken out from the hole portion 29 by the simple operation to unravel the securing part 11 and to pull the fixing part 12.

When the organ fixing equipment 10 is to be attached to the abdomen of the patient, according to the organ fixing equipment set of the invention, the piercing needle 21 of the insertion equipment 20 is pierced, while the securing part 11 and the fixing part 12 being partially accommodated in the piercing needle 21, into the abdomen of the patient so that the securing part 11 can be inserted into the stomach wall B. While the portion of the piercing needle 21 on the side of the leading end portion 25 being left in the stomach wall B, moreover, the securing part 11 is pushed out from the piercing needle 21 by the cylindrical protrusion portion 22 and the insertion equipment 20 is pulled out from the body of the patient so that the organ fixing equipment 10 can be attached. Thus, the organ fixing equipment 10 can be attached to the body of the patient by the simple operations.

According to the organ fixing equipment set of the invention, moreover, the organ fixing equipment 10 can be taken out from the abdomen of the patient by the simple operations using the taking-out equipment 30. Specifically, the exposed portion of the fixing part 12 is inserted, while being wound on the circumference of the cylindrical portion 32 of the taking-out equipment 30, into the grip portion 34, and the cylindrical portion 32 is inserted into the hole portion 29. While the leading end portion of the cylindrical portion 32 being applied to the securing part 11, the fixing part 12 is pulled so that the organ fixing equipment 10 can be simply taken out.

Figure 17:
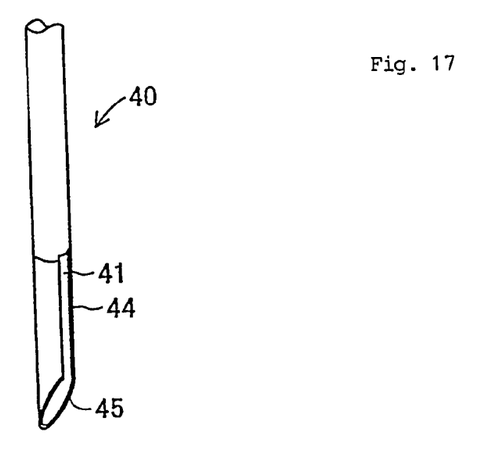
FIG. 17 is a perspective view showing an insertion equipment used in the organ fixing equipment set according to another embodiment.

On the other hand, FIG. 17 shows an insertion equipment 40 to be used in an organ fixing equipment set according to another embodiment of the invention. This insertion equipment 40 is made of a cylinder member having a bore 41 formed therein, and its leading end portion 45 is cut sharp in a direction oblique to the axial direction. Moreover, a groove portion 44 is formed to extend straight from the upper end portion of the opening of the leading end portion 45 toward the upper portion side of the insertion equipment 40. When the organ fixing equipment 10 is to be attached to the body of the patient by using that insertion equipment 40, the securing part 11 is inserted, while the fixing part 12 being left outside, into the groove portion 44 from the leading end portion 45 of the insertion equipment 40. Then, the insertion equipment 40 is pierced into the body of the patient, and the securing part 11 is pushed into the stomach wall B. The organ fixing equipment 10 can be attached by pulling the insertion equipment 40 from the body of the patient. The organ fixing equipment 10 can also be easily and reliably attached by the insertion equipment 40.

In a still another embodiment, the suturing thread forming the securing part 11 of the organ fixing equipment 10 can also be fixed with an adhesive made of such a bio-absorptive material as will disappear after lapse of a predetermined time period when buried in the human body. In this case, the securing part 11 is slackened and unraveled at the lapse of the predetermined time period after the organ fixing equipment 10 was attached. Not by using the taking-out equipments 30 and 40 but merely by pulling the fixing part 12, therefore, the organ fixing equipment 10 can be taken out from the body.

On the other hand, the organ fixing equipment and the organ fixing equipment set according to the invention should not be limited to the embodiments thus far described but can be practiced in suitable modifications. In the foregoing embodiments, for example, the suturing thread forming the organ fixing equipment 10 is made of nylon, but its material should not be limited to nylon. The suturing thread may be made of polyester, silk, polyolefin or a bio-absorptive material, for example. Moreover, the bundling method of the securing part 11 should not be limited to that of the foregoing embodiments but may be any if it can form the securing part 11 into a bar shape.

In this modification, the securing part 11 may be formed into the bar shape by using an adhesive of the bio-absorptive material or the like. Moreover, the constitutions of the shapes and materials of the insertion equipment and the taking-out equipment can also be suitably modified. For example, the material for making the insertion equipment may be stainless steel, Nitinol or titanium. Moreover, the material for making the taking-out equipment may be a metallic material such as stainless steel, Nitinol or titanium, or a resin material such as polycarbonate, nylon or a fluorine-containing resin. Moreover, the organ fixing equipment and the organ fixing equipment set of the invention can be employed for suturing not only the abdomen wall A and the stomach wall B but also another portion in the body, such as kidney or bladder.

At least one of the above-described embodiments of the present invention provides an organ fixing equipment capable of fixing an organ reliably by a simple operation, and a set of the organ fixing equipment.

According to at least one embodiment of the invention, there is provided an organ fixing equipment for fixing a predetermined organ in the body of a patient, on a skin side wall portion. The organ fixing equipment comprises: a securing part formed by bundling a suturing thread into a bar and adapted to be disposed on the inner wall side of the organ; and a fixing part having the suturing thread forming the securing part and a continuous suturing thread and extending to the outside of the body of the patient from the substantial center in the axial direction of the securing part through a hole portion formed in the organ and in the skin side wall portion.

The organ fixing equipment thus constituted according to at least one embodiment of the invention comprises: the bar-shaped securing part disposed on the inner wall side of the organ; and the fixing part extending from the substantial center of the securing part to the outside through the hole portion formed in the patient. Here, the substantial center along the axial direction of the securing part is located at such a substantial center in the longitudinal direction that the securing part is opened with respect to the fixing part when the securing part is positioned in the organ. When the securing part is positioned in the organ through the hole portion, therefore, the securing part extends along the inner wall of the organ, so that the securing part and the fixing part take a shape of letter "T" thereby to fix the organ and the skin side wall portion. As a result, the constitution of the organ fixing equipment is simplified, and the operation for attaching the organ fixing equipment is remarkably simplified.

Moreover, the securing part is formed into the bar shape by bundling the suturing thread. Therefore, the organ fixing equipment can be simply taken out from the hole portion by unraveling the securing part and by pulling the fixing part. In this case, for example, a bio-absorptive material can be used as an adhesive to form the securing part into the bar shape. According to this modification, when a predetermined time period elapses after the securing part was disposed in a predetermined organ in the body, the securing part becomes unraveled. If, therefore, a predetermined disposal of attaching another medical tool such as the gastrostomy tube is ended for the lapse time, the organ fixing tool may be taken out merely by pulling the fixing part.

Moreover, the organ fixing equipment can also be constituted such that the suturing thread forming the securing part can be unraveled by pulling the fixing part relative to the securing part with a force of not less than a predetermined magnitude. The force not less than the predetermined magnitude in this case is stronger than the force for the securing part to fix the organ. Moreover, the force may also be stronger than the force for the securing part to fix the organ only for a constant time period after the securing part fixed the organ, and either a force weaker than that for fixing the organ or a force near "0" after the constant time period. According to this, the taking-out operation to take out the organ fixing equipment after a medical equipment such as the gastrostomy tube was attached can be facilitated and made reliable.

Another constitutional characteristic of the organ fixing equipment according to at least one embodiment of the invention is that the securing part includes: a core portion formed by bundling the suturing thread in a manner to fold it back at a predetermined length a plurality of times; and a coil portion formed by winding the suturing thread around the core portion. According to this characteristic, it is easy to manufacture the organ fixing equipment and to unravel the securing part.

A constitutional characteristic of the organ fixing equipment set according to the at least one embodiment of invention is that it comprises an organ fixing equipment, and an insertion equipment to be used when the organ fixing equipment is to be attached to the organ; and in that the insertion equipment includes a member which can be inserted into the body of the patient in the state where the securing part of the organ fixing equipment is accommodated, and which can be pulled out from the patient in the state where the securing part is left inside of the organ. The insertion equipment of this case may be constituted of either a needle to be pierced into the body of the patient or a cylindrical member, which has a non-sharp leading end portion but can be inserted into a hollow portion formed in advance in the body of the patient. According to this constitution, it is easy to attach the organ fixing equipment to the inside of the organ.

Another constitutional characteristic of the organ fixing equipment set according to at least one embodiment of the invention is that it comprises an organ fixing equipment, and a taking-out equipment to be used when the organ fixing equipment is to be taken out from the organ, and in that the taking-out equipment includes a cylindrical portion which can insert at least a portion of the fixing part, while accommodating it, into the hole portion, and which can extract the fixing part from the hole portion after the fixing part was pulled to unravel the securing part while the leading end portion being applied to the securing part. According to this constitution, it is easy to take out the organ fixing equipment.

Another constitutional characteristic of the organ fixing equipment set according to at least one embodiment of the invention is that the taking-out equipment includes a cylindrical portion and a grip portion disposed at the base end portion of the cylindrical portion, and in that a helical groove portion extending in the axial direction while turning in the circumferential direction from the leading end portion to the base end side portion of the cylindrical portion is formed through the cylindrical portion between the outer circumference and the inner circumference. According to this constitution, the taking-out equipment can be inserted, while being turned to bring the fixing part into the groove portion, into the body of the patient and is pushed at its leading end portion onto the boundary between the securing part and the fixing part, so that the securing part can be taken out, while being unraveled, to the outside of the body of the patient.

Having described the invention in detail, it will be apparent that modifications and variations are possible without departing from the scope of the invention defined in the appended claims.

When introducing elements of the present invention or the illustrated embodiment(s) thereof, the articles "a", "an", "the" and "said" are intended to mean that there are one or more of the elements. The terms "comprising", "including" and "having" are intended to be inclusive and mean that there may be additional elements other than the listed elements.

As various changes could be made in the above constructions, products, and methods without departing from the scope of the invention, it is intended that all matter contained in the above description and shown in the accompanying drawings shall be interpreted as illustrative and not in a limiting sense.

The invention claimed is:

1. An organ fixing device, comprising
a suture thread having a first end portion, a second end portion and an intermediate portion connecting the first end portion to the second end portion, the first end portion defining a pulling part, the intermediate portion and the second end portion defining a securing part, wherein the intermediate portion of the suture thread comprises a plurality of folded segments and the second end portion of the suture thread comprises a plurality of coiled segments, and wherein each of the coiled segments is disposed around the plurality of folded segments, wherein the plurality of coiled segments define a coil portion having opposite longitudinal ends, the pulling part being connected to the intermediate portion of the suture thread at a location intermediate the opposite longitudinal ends of the coil portion.

2. The device of claim 1, wherein the securing part comprising the intermediate and second end portions of the suture thread defines a bar having a longitudinal center, and wherein the location where the pulling part is connected to the intermediate portion of the suture thread is at the longitudinal center of the bar.

3. The device of claim 1, wherein the location where the pulling part is connected to the intermediate portion of the suture thread is between adjacent coiled segments of the plurality of coiled segments.

4. The device of claim 1, wherein the suture thread is T-shaped, the pulling part extending perpendicularly from the securing part.

5. The device of claim 1, wherein the securing part is configured such that when the pulling part is pulled relative to the securing part with at least a predetermined force, the folded segments being sequentially withdrawn from the coil portion so that the securing part unravels.

6. The device of claim 1, in combination with insertion equipment for use in inserting the securing part of the suture thread in a stomach of a subject, the insertion equipment including a piercing needle configured for piercing abdomen and stomach walls of the subject, the piercing needle defining a passage configured for receiving the securing part of the suture thread to facilitate delivery of the securing part of the suture thread through the abdomen and stomach walls of the subject and into the stomach of the subject.

7. The device of claim 6, wherein the insertion equipment further includes a protrusion portion having a cylindrical member configured for reception in the passage of the piercing needle to facilitate delivery of the securing part of the suture thread into the stomach of the subject through the passage of the piercing needle.

8. The device of claim 6, in further combination with taking-out equipment for removing the organ fixing device from the subject, the taking-out equipment including a cylindrical portion having a helical groove for receiving the suture thread of the organ fixing device.

* * * * *

UNITED STATES PATENT AND TRADEMARK OFFICE
CERTIFICATE OF CORRECTION

| | | |
|---|---|---|
| PATENT NO. | : 8,663,278 B2 | Page 1 of 1 |
| APPLICATION NO. | : 11/576873 | |
| DATED | : March 4, 2014 | |
| INVENTOR(S) | : Mabuchi et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1547 days.

Signed and Sealed this
Twenty-second Day of September, 2015

Michelle K. Lee
*Director of the United States Patent and Trademark Office*